United States Patent [19]

Olesen et al.

[11] Plant 4,939

[45] Nov. 16, 1982

[54] ROSE PLANT

[76] Inventors: Pernille Olesen; Mogens Olesen, both of 58 Kelleriisvej, DK 3490 Kvistgaard, Denmark

[21] Appl. No.: 274,801

[22] Filed: Jun. 18, 1981

[51] Int. Cl.[3] ..... A01H 5/00

[52] U.S. Cl. ..... Plt./9

[58] Field of Search ..... Plt./7, 9

*Primary Examiner*—Robert E. Bagwill
*Attorney, Agent, or Firm*—Vincent G. Gioia

[57] ABSTRACT

A new Spinel red miniature rose which lightens to light pink tonality upon aging.

1 Drawing Figure

1

The present invention relates to a new and distinct variety of rose plant of the miniature rose class, which was originated by my crossing as seed parent the rose known as "Mini Poul" and the rose known as "Harriet Poulsen" as pollen parent.

Among the novel characteristics possessed by this new variety which distinguish it from its parents and all other varieties of which I am aware are unusual Spinel red flower coloring, blooms borne singly and 3 to 4 to a stem if not disbudded in a manner typical of hybrid teas and an upright, vigorous plant of excellent disease resistance and winter hardiness. Asexual reproduction by budding of the new variety as performed in Clackamas County, Oreg., shows that the foregoing and other distinguishing characteristics come true to form and are established and transmitted through succeeding propagations.

The new and improved rose variety which I have developed is an unusual miniature rose in its coloring combining attractive flowers and verdant foliage. Like many hybrid teas, the flowers may be both singly-borne and in small clusters displayed on long stems. The changing colors upon aging result in an eye-catching plant for display with varying pink color tones often visible at the same time.

The accompanying drawing shows typical specimens of the vegetative growth and flowers of the new variety in different stages of development and as depicted in color as nearly true as it is reasonably possible to make the same in color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "51B" is plate 51B of the Royal Horticultural Society Color Chart.

Parentage: Seedling.
*Seed parent.*—"Mini Poul".
*Pollen parent.*—"Harriet Poulsen".
Class: Miniature.

The following observations are made of specimens grown under glass in Clackamas County, Oreg., during the month of January.

FLOWER

Blooming habit: Continuous.

2

A. Bud:
(1) *Size.*—Small.
(2) *Form.*—Ovate.
(3) *Color.*—As sepals divide, color of bud is Rhodonite red 51B. Freshly unfurled petals (top surface) appear Spinel red 54C.
(4) *Sepals.*—Simple, acuminate, longer than bud, pilose inside, glabrous outside.
(5) *Peduncle.*—Length — about 30–40 mm. Aspect — upright. Strength — erect. Color — 143C.

B. Bloom:
(1) *Size.*—Average size when fully expanded — about 25 mm.
(2) *Borne.*—Singly and in sprays of 3–4 blooms.
(3) *Form.*—Cupped, high centered, reflexing at maturity.
(4) *Petalage.*—Number of petals under normal conditions — about 25 to 30.
(5) *Color.*—Ovate buds opening to one-half-open stage appear between 54B and 54C. As flower opnes further, light yellow, 11C, point of petal attachment is seen emphasized by the yellow pollen coloring visible in the open bloom. As flower ages, petal section near point of attachment whitens with pink shading into darker pink petal edges. Pink shading color is near to 56B washing into 55B toward petal edge. General tonality after several days is light pink.

C. Petals:
(1) *Texture.*—Relatively thick.
(2) *Appearance.*—Inside — velvety; Outside — satiny.
(3) *Form.*—Usually rounded at outer edge, sometimes reflexing to a point, sometimes folding under.
(4) *Arrangement.*—Shingle-like.
(5) *Petaloids in center.*—Few.
(6) *Persistence.*—Drop cleanly.
(7) *Fragrance.*—Light, fruity.
(8) *Lasting quality.*—Long on plant and as cut flower.

REPRODUCTIVE ORGANS

A. Stamens, filaments and anthers:
(1) *Arrangement.*—Regular, outer stamens incurved.
(2) *Color.*—11B.

B. Pollen:
*Color.*—11C.

C. Styles: Few, 12–15, even length, tightly bunched.

D. Stigmas:
*Color.*—8D.

E. Hips: Oval, long, sepals persist, 5 mm × 2 mm.
*Color.*—150B, seeds do not protrude.

PLANT

A. Form: Upright, compact.

B. Growth: Vigorous, uniform.
*Height attained.*—30–40 mm.

C. Foliage: Compound 5 leaflet leaves.
(1) *Size.*—Small, 1 to 1.5 cm.
(2) *Quantity.*—Abundant, close set.
(3) *Color.*—Upper side — near 137B. Under side — near 137B.
(4) *Shape.*—Ovate, acuminate.
(5) *Texture.*—Upper side — shiny. Under side — satiny.
(6) *Edge.*—Serrated.
(7) *Serration.*—Simple.
(8) *Leaf stem.*—Color — near to 146C. Under Side — near to 146C.
(9) *Stipules.*—Short, broad, pointed.

(10) *Resistance to Disease.*—Blackspot — excellent. Mildew — excellent. Rust — excellent.

D. Wood:
(1) *New wood.*—Color — near 143C. Bark — smooth.
(2) *Old wood.*—Color — near to 144A. Bark — smooth.

E. Thorns:
(1) *Thorns.*—Quantity — few, scattered. On laterals from stalk — few. Form — straight, pointed. Length — short, 3 mm. Color (when young) — 51A. Position — irregular.
(2) *Prickles.*—None.

F. Winter hardiness: Very hardy.

We claim:

1. A new and distinct variety of rose plant of the miniature class, substantially as shown and described, characterized particularly by Rhodonite red buds opening to Spinel red flowers borne on an upright plant of excellent disease resistance and winter hardiness.

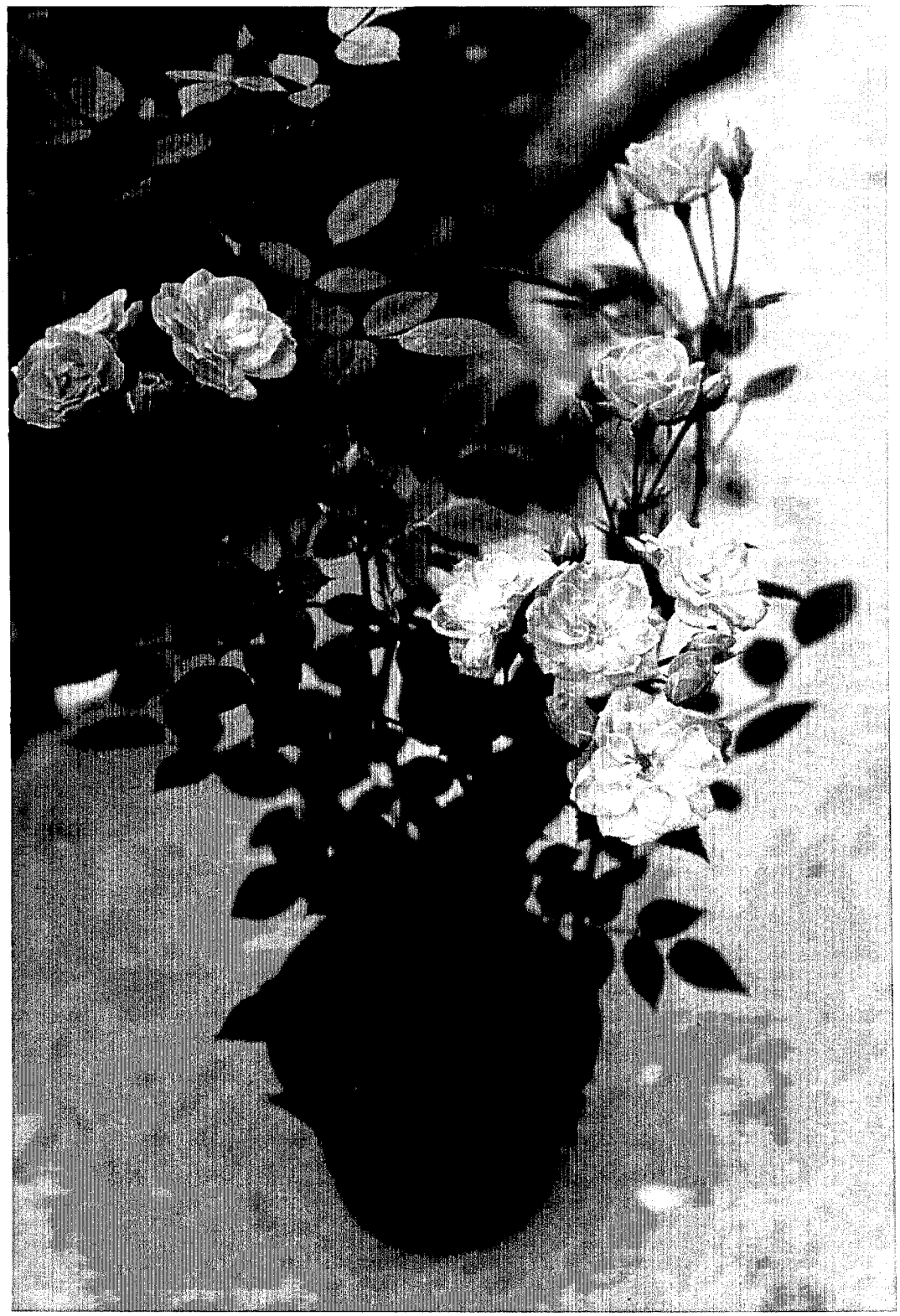

* * * * *